United States Patent
Li

(10) Patent No.: US 6,784,326 B1
(45) Date of Patent: Aug. 31, 2004

(54) PROCESS FOR IMPROVING STABILITY OF GLYCERIN

(75) Inventor: Thomas Z. Li, Cincinnati, OH (US)

(73) Assignee: Cognis Corporation, Cincinnati, OH (US)

( * ) Notice: Subject to any disclaimer, the term of this patent is extended or adjusted under 35 U.S.C. 154(b) by 867 days.

(21) Appl. No.: 09/098,679

(22) Filed: Jun. 17, 1998

(51) Int. Cl.⁷ ......................... C07C 31/18; C07C 29/00; C07C 27/00
(52) U.S. Cl. ....................... 568/852; 568/869
(58) Field of Search ................................ 568/852, 869

(56) References Cited

U.S. PATENT DOCUMENTS 5,134,130 A * 7/1992 Shaw et al. .................... 514/78

FOREIGN PATENT DOCUMENTS

JP 06184024 * 7/1994

OTHER PUBLICATIONS

Turanskii et al, "Automatic Control of the Purification of Spent Lyes", Maslo–Zhir, Prom., Issued 1971, vol. 37, No. 11, pp. 20–21.*

* cited by examiner

Primary Examiner—James O. Wilson
Assistant Examiner—Everett White
(74) Attorney, Agent, or Firm—Aaron R. Ettelman; Steven J. Trzaska

(57) ABSTRACT

A process for inhibiting the oxidative degradation of glycerin involving adjusting the pH of glycerin to a range of either: (a) from about 3.5 to about 5.0; or (b) to from about 10.0 to about 12.0.

16 Claims, No Drawings

PROCESS FOR IMPROVING STABILITY OF GLYCERIN

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Glycerol, propane-1,2,3-triol, glycerin (USP), is a trihydric alcohol having a sweet taste, is a clear, water-white viscous, hygroscopic liquid at ordinary room temperatures, which are above its melting point. Glycerin occurs naturally in combined form as glycerides in all animal and vegetable fats and oils, and is recovered as a by-product when these oils are saponified in the process of manufacturing soap, or during the direct splitting of fats in the production of fatty acids. Since 1949 it has also been produced commercially by synthesis from propylene.

The uses of glycerin number in the thousands but the majority of uses relate to the manufacture of synthetic resins and ester gums, drugs, cosmetics, and toothpastes. In the production of alkyd resins, glycerin is employed as a reactive polyol in many formulations. Because of the polyfunctional nature of glycerin, polymer building reactions with difunctional organic acids occur readily. These glycerin based polymers are generally modified further by the addition of monobasic organic acids to achieve resins with either air cure or heat cure properties.

The cosmetic industry has for many years used glycerin in various creams and lotions to keep the skin soft and moist. In addition, glycerin is used in a variety of personal care products such as mouthwash, toothpaste and shampoos where the glycerin serves as a solubilizer and viscosity modifier in the formulation. Glycerin is generally considered to be a flavor enhancer in mouthwash and toothpaste products in contrast to other polyol types which require masking of their particular taste characteristics.

The pharmaceutical industry uses glycerin extensively as a solvent and solubilizer in various drug vehicles for both internal and external uses.

Glycerin is employed as a humectant in tobacco processing. Furthermore, in the food and beverage industry, glycerin is used as a solvent for food flavoring and coloring. Food grade fatty acid esters of glycerin are used extensively in food preparations requiring emulsification.

Glycerin and glycerin derivatives continue to be used extensively in soaps and detergents, hair care products, chewing gum base, lubricants, glass and ceramics and a variety of adhesives.

Glycerin is completely soluble in water and alcohol, slightly soluble in diethyl ether, ethyl acetate and dioxane, and insoluble in hydrocarbons. Glycerin is used to form esters, ethers, halides, amines, aldehydes, and such unsaturated compounds as acrolein. As an alcohol, glycerin also has the ability to form salts such as sodium glyceroxide.

Glycerin derivates include acetals, amines, esters and ethers, the esters being the most widely used. Commercially, the most important are the alkyd resins, which are esters of glycerin and pthalic anhydride.

One of the drawbacks associated with the use of glycerin relates to its susceptibility to color degradation. Glycerin, when exposed to high temperatures such as those associated with the formation of various finished products containing glycerin such as, for example, soap, cosmetics, and the like, has a tendency to thermally degrade, causing colored by-products to form. In many applications associated with the use of glycerin, it is oftentimes desirable for it to remain as color-free as possible.

BRIEF SUMMARY OF THE INVENTION

The present invention is directed to a process for inhibiting thermal degradation of glycerin involving adjusting the pH of glycerin to either: (a) from about 3.5 to about 5 or (b) to above about 10.

BRIEF DESCRIPTION OF THE SEVERAL VIEWS OF THE DRAWING

Not applicable.

DETAILED DESCRIPTION OF THE INVENTION

Other than in the operating examples, or where otherwise indicated, all numbers expressing quantities of ingredients or reaction conditions, are understood as being modified in all instances by the term "about".

The glycerin component employed in the present invention may be derived by a number of various methods. It may be obtained as a by-product in soap manufacture; by reacting propylene and chlorine to form allyl chloride which is then converted to dichlorohydrin with hypochlorous acid, which is then saponified to glycerin with a caustic solution. Other methods of derivation include the isomerization of propylene oxide to allyl alcohol, which is then reacted with peracetic acid, the resulting glycidol being hydrolyzed to glycerin; and hydrogenation of carbohydrates with a nickel catalyst.

The oxidative degradation of glycerin typically occurs in one of two ways. Upon prolonged storage, two hydrogen atoms of the glycerin tend to lose two electrons via a catalytic reaction with air or oxygen. This, in turn, causes the glycerin to become discolored which is clearly an unwanted phenomenon.

The exposure of glycerin to elevated temperatures, such as those employed in many finished good processing applications, also results in oxidative degradation. Elevated temperatures cause electrons to become displaced within the molecule, resulting in the formation of unwanted color bodies in the glycerin.

The stability of glycerin may be enhanced, however, by using either an acid or a base, in order to adjust its pH within a certain range. According to one embodiment of the present invention, glycerin is stabilized, thereby inhibiting its oxidative degradation, by adjusting its pH to a range of either from about 4 to about 5.5, and preferably from about 4.5 to about 5.0 using a dilute acid. Suitable acids include, but are not limited to, hydrochloric, nitric and sulfuric acids. Weak acids such as acetic and carbonic acids may also be employed.

According to another embodiment of the present invention, glycerin may also be stabilized by adjusting its pH to a range of greater than about 10, and preferably from about 11.0 to about 12.0 by using a dilute base. Suitable bases include, but are not limited to, water-soluble hydroxides such as sodium, potassium and ammonium hydroxide.

It should be noted, however, that any type of acid or base may be used, so long as it is capable of adjusting the pH of glycerin within the above-disclosed ranges.

The present invention will be better understood from the examples which follow, all of which are intended to be illustrative only and are not meant to unduly limit the scope of the invention in any way.

EXPERIMENTAL (A) A 25.0 gram sample of glycerine was dissolved in 75 grams of distilled water. While stirring, a 0.1% NaOH solution was added in small increments through a buret into the sample solution. The corresponding PH changes were measured with a Fisher Scientific Model 50 Accumet PH Meter.

TABLE (a)

| 0.1% NaOH(ml.) | PH Change |
|---|---|
| 0 | 5.90 |
| 0.10 | 7.00 |
| 0.25 | 8.23 |
| 0.30 | 8.50 |
| 0.40 | 8.87 |
| 0.50 | 9.07 |
| 0.65 | 9.25 |
| 1.00 | 9.50 |
| 1.65 | 9.81 |
| 2.30 | 9.98 |
| 2.35 | 9.99 |
| 2.45 | 10.00 |
| 2.50 | 10.00 |
| 4.10 | 10.25 |
| 7.10 | 10.50 |
| 7.20 | 10.50 |
| 10.00 | 10.66 |
| 12.55 | 10.75 |
| 20.00 | 10.96 |
| 21.85 | 11.00 |
| 21.95 | 11.00 |
| 22.10 | 11.00 |
| 22.25 | 11.00 |
| 28.50 | 11.10 |
| 30.00 | 11.13 |

(B) A 25.0 gram sample of glycerine was dissolved in 75 grams of distilled water. While stirring, a 0.01% $H_2SO_4$ solution was added in small increments through a buret into the sample solution. The corresponding pH changes were measured with a Fisher Scientific Model 50 Accumet PH Meter.

TABLE (b)

| ml. of 0.01% $H_2SO_4$ | pH change | ml. of 0.01% $H_2SO_4$ | pH change |
|---|---|---|---|
| 0.00 | 5.97 | 3.05 | 4.30 |
| 0.30 | 5.68 | 3.25 | 4.26 |
| 0.35 | 5.64 | 3.30 | 4.25 |
| 0.42 | 5.60 | 3.55 | 4.20 |
| 0.55 | 5.48 | 3.85 | 4.15 |
| 0.65 | 5.39 | 4.20 | 4.10 |
| 0.75 | 5.31 | 4.60 | 4.05 |
| 0.80 | 5.27 | 5.05 | 3.99 |
| 0.85 | 5.23 | 5.50 | 3.95 |
| 0.90 | 5.19 | 5.90 | 3.91 |
| 1.00 | 5.10 | 6.00 | 3.90 |
| 1.05 | 5.06 | 6.60 | 3.85 |
| 1.10 | 5.03 | 7.35 | 3.80 |
| 1.13 | 5.00 | 8.15 | 3.75 |
| 1.20 | 4.95 | 8.95 | 3.70 |
| 1.30 | 4.89 | 10.05 | 3.65 |
| 1.40 | 4.84 | 11.05 | 3.60 |
| 1.45 | 4.81 | 12.40 | 3.55 |
| 1.50 | 4.79 | 13.90 | 3.50 |
| 1.60 | 4.74 | 15.70 | 3.45 |
| 1.65 | 4.72 | 17.75 | 3.40 |
| 1.70 | 4.70 | 20.00 | 3.36 |
| 1.80 | 4.66 | 20.20 | 3.35 |
| 1.91 | 4.60 | 23.15 | 3.30 |
| 2.05 | 4.55 | 26.66 | 3.25 |
| 2.20 | 4.51 | 30.00 | 3.22 |
| 2.25 | 4.49 | 30.87 | 3.20 |
| 2.40 | 4.46 | 36.40 | 3.15 |
| 2.58 | 4.41 | 40.00 | 3.12 |
| 2.61 | 4.40 | 43.00 | 3.00 |
| 2.75 | 4.36 | 49.00 | 2.95 |
| 2.75 | 4.36 | 56.50 | 2.90 |
| 3.00 | 4.31 | 66.00 | 2.85 |

TABLE I

Preparation of glycerine samples of PH = 8.0 to 11.0 based on results obtained on (3722-76) Table (a)
Preparation of 300.0 g. samples of glycerine

| No. 3722-77 | PH Cal-culated | PH Exp. | 25 g of glycerine 0.1% NaOH needed based on 3722-76 | 0.1% NaOH (ml.) | 1.0% NaOH (ml.) | 10% NaOH (ml.) |
|---|---|---|---|---|---|---|
| A | 8.00 | 8.04 | 0.24 | 0.88 | 0.20 | 0 |
| B | 8.50 | 8.55 | 0.30 | 0.60 | 0.30 | 0 |
| C | 9.00 | 9.03 | 0.65 | 0.80 | 0.70 | 0 |
| D | 9.25 | 9.29 | 1.00 | 0 | 1.20 | 0 |
| E | 9.50 | 9.55 | 1.34 | 0.08 | 0.60 | 0.10 |
| F | 9.75 | 9.78 | 2.50 | 0 | 0 | 0.30 |
| G | 10.00 | 10.00 | 4.10 | 0.20 | 0.90 | 0.40 |
| H | 10.25 | 10.25 | 4.10 | 0.20 | 0.90 | 0.40 |
| I | 10.50 | 10.51 | 7.20 | 0.40 | 0.60 | 0.80 |
| J | 10.75 | 10.75 | 12.55 | 0.60 | 0 | 1.50 |
| K | 11.00 | 11.00 | 22.18 | 0.20 | 0.60 | 2.60 |

TABLE II

Preparation of glycerine samples of PH = 5.0 to 2.9 based on results obtained on 3722-78 and 3722-79; Table (b)
Preparation of 350.0 g. samples of glycerine

| No. 3722-80 | PH Cal-culated | PH Exp. | 25 g of gly. 0.1% $H_2SO_4$ needed based on 3722-78 & 79 | 00.1% $H_2SO_4$ (ml.) | 0.1% $H_2SO_4$ (ml.) | 1.0% $H_2SO_4$ (ml.) |
|---|---|---|---|---|---|---|
| A | 5.00 | 5.05 | 1.13 | 0.82 | 1.50 | 0 |
| B | 4.90 | 4.97 | 1.28 | 0.92 | 1.70 | 0 |
| C | 4.80 | 4.88 | 1.475 | 0.65 | 2.00 | 0 |
| D | 4.70 | 4.76 | 1.70 | 0.80 | 2.30 | 0 |
| E | 4.60 | 4.71 | 1.91 | 0.15 | 0.10 | 0.20 |
| F | 4.50 | 4.52 | 2.225 | 0.15 | 0.10 | 0.30 |
| G | 4.40 | 4.55 | 2.61 | 0.54 | 0.60 | 0.30 |
| H | 4.30 | 4.37 | 3.05 | 0.70 | 0.20 | 0.40 |
| I | 4.20 | 4.22 | 3.55 | 0.70 | 0.90 | 0.40 |
| J | 4.10 | 4.11 | 4.20 | 0.80 | 0.80 | 0.50 |
| K | 4.10 | 4.14 | 4.58 | 0.17 | 0.40 | 0.60 |
| L | 4.00 | 4.02 | 5.05 | 0.70 | 0 | 0.70 |
| M | 3.90 | 3.99 | 6.00 | 0 | 0.40 | 0.80 |
| N | 3.80 | 3.94 | 7.35 | 0.90 | 0.20 | 1.00 |
| O | 3.70 | 3.88 | 8.95 | 0.30 | 0.50 | 1.20 |

TABLE II-continued

Preparation of glycerine samples of PH = 5.0 to 2.9 based on results obtained on 3722-78 and 3722-79; Table (b)
Preparation of 350.0 g. samples of glycerine

| No. 3722-80 | PH Cal- culated | PH Exp. | 25 g of gly. 0.1% $H_2SO_4$ needed based on 3722-78 & 79 | 00.1% $H_2SO_4$ (ml.) | 0.1% $H_2SO_4$ (ml.) | 1.0% $H_2SO_4$ (ml.) |
|---|---|---|---|---|---|---|
| P | 3.60 | 3.75 | 11.05 | 0.70 | 0.40 | 1.50 |
| Q | 3.50 | 3.63 | 13.90 | 0.60 | 0.40 | 1.90 |
| R | 3.40 | 3.51 | 17.75 | 0.50 | 0.80 | 2.40 |
| S | 3.30 | 3.41 | 23.15 | 0 | 0.90 | 3.20 |
| T | 3.20 | 3.28 | 30.87 | 0.20 | 0.20 | 4.30 |
| U | 3.10 | 3.15 | 41.20 | 0.80 | 0.60 | 5.70 |
| V | 3.00 | 3.12 | 43.0 | 0 | 0.20 | 6.00 |
| W | 2.90 | 2.97 | 56.5 | 0 | 0.10 | 7.90 |

TABLE III

Thermal stability of glycerine at pH = 8.0 to 11.0

| No. 3722-77 | PH Calculated | PH Experimental | Thermal stability 2-hr. @ 205° C. in the presence of air % T @ 440/550 nm |
|---|---|---|---|
| Control |  | 5.9 | 78/90 |
| A | 8.00 | 8.04 | 65/90 |
| B | 8.50 | 8.55 | 72/92 |
| C | 9.00 | 9.03 | 75/94 |
| D | 9.25 | 9.29 | 75/95 |
| E | 9.50 | 9.55 | 81/96 |
| F | 9.75 | 9.78 | 81/95 |
| G | 10.00 | 10.00 | 84/96 |
| H | 10.25 | 10.25 | 90/98 |
| I | 10.50 | 10.51 | 91/98 |
| J | 10.75 | 10.75 | 94/99 |
| K | 11.00 | 11.00 | 95/99 |

TABLE IV

Thermal stability of glycerine at pH = 5.0 to 2.9

| No. 3722-77 | PH Calculated | PH Experimental | Thermal stability 2-hr. @ 205° C. in the presence of air % T @ 440/550 nm |
|---|---|---|---|
| Control |  | 5.9 | 78/90 |
| A | 5.00 | 5.05 | 86/97 |
| B | 4.90 | 4.97 | 87/98 |
| C | 4.80 | 4.88 | 88/98 |
| D | 4.70 | 4.76 | 90/99 |
| E | 4.60 | 4.71 | 88/98 |
| F | 4.50 | 4.52 | 86/97 |
| G | 4.40 | 4.55 | 88/98 |
| H | 4.30 | 4.37 | 87/97 |
| I | 4.20 | 4.22 | 90/97 |
| J | 4.10 | 4.11 | 91/98 |
| K | 4.10 | 4.14 | 91/98 |
| L | 4.00 | 4.02 | 91/98 |
| M | 3.90 | 3.99 | 90/97 |
| N | 3.80 | 3.94 | 88/95 |
| O | 3.70 | 3.88 | 88/96 |
| P | 3.60 | 3.75 | 86/95 |
| Q | 3.50 | 3.63 | 83/95 |
| R | 3.40 | 3.51 | 76/93 |
| S | 3.30 | 3.41 | 37/85 |
| T | 3.20 | 3.28 | 20/72 |
| U | 3.10 | 3.15 | 6/53 |
| V | 3.00 | 3.12 | 4/40 |
| W | 2.90 | 2.97 | 2/28 |

As can be seen from the data in the tables above, by adjusting the pH of glycerin to within the above-disclosed ranges, the stability of glycerin as it relates to oxidative degradation is significantly enhanced.

What is claimed is:

1. A process for inhibiting the oxidative degradation of glycerin comprising adjusting the pH of glycerin to a range of from about 3.5 to about 5.0.

2. The process of claim 1 wherein the pH is adjusted to from about 4.0 to about 5.0.

3. The process of claim 1 wherein the pH is adjusted by adding an acid to the glycerin.

4. The process of claim 3 wherein the acid is sulfuric acid.

5. A process for inhibiting the oxidative degradation of glycerin comprising adjusting the pH of glycerin to a range of from about 10.0 to about 12.0.

6. The process of claim 5 wherein the pH is adjusted to a range of from about 11.0 to about 12.0.

7. The process of claim 5 wherein the pH is adjusted by adding a base to the glycerin.

8. The process of claim 7 wherein the base is sodium hydroxide.

9. The product of the process of claim 1.
10. The product of the process of claim 2.
11. The product of the process of claim 3.
12. The product of the process of claim 4.
13. The product of the process of claim 5.
14. The product of the process of claim 6.
15. The product of the process of claim 7.
16. The product of the process of claim 8.

\* \* \* \* \*